(12) United States Patent
Cewers et al.

(10) Patent No.: US 6,371,115 B1
(45) Date of Patent: Apr. 16, 2002

(54) DEVICE FOR THE SUPPLY OF A GAS FROM A RESPIRATOR/ANAESTHESIA DEVICE TO A BEDRIDDEN PATIENT

(75) Inventors: Göran Cewers, Lund; Christer Ström, Piteå, both of (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/512,041

(22) Filed: Feb. 24, 2000

(30) Foreign Application Priority Data

Feb. 26, 1999 (SE) .............................................. 9900704

(51) Int. Cl.⁷ ............................................ A61M 16/00
(52) U.S. Cl. ............................ 128/204.23; 128/202.22; 128/205.23
(58) Field of Search ....................... 128/204.23, 202.22, 128/200.24, 205.23

(56) References Cited

U.S. PATENT DOCUMENTS

| | | |
|---|---|---|
| 3,236,236 A | 2/1966 | Hudson |
| 4,584,989 A | 4/1986 | Stith |
| 4,821,736 A * | 4/1989 | Watson ........................ 128/719 |
| 4,860,764 A * | 8/1989 | Hudimac, Jr. ............... 128/725 |
| 5,497,766 A | 3/1996 | Foster et al. |
| 5,970,975 A * | 10/1999 | Estes et al. ............. 128/204.23 |
| 6,213,955 B1 * | 4/2001 | Karakasoglu et al. ....... 600/529 |
| 6,269,811 B1 * | 8/2001 | Duff et al. ............. 128/204.21 |

FOREIGN PATENT DOCUMENTS

WO    WO 98/48878    11/1998

* cited by examiner

Primary Examiner—John G. Weiss
Assistant Examiner—Mital Patel
(74) Attorney, Agent, or Firm—Schiff Hardin & Waite

(57) ABSTRACT

A device for the supply of a gas from a respirator/anaesthesia device to a bedridden patient has at least one gas tube and a connecting interface, which can be connected to the patient, and an adjustable holding device for the gas tube and for the connecting interface. In order to prevent leaks, injury to the patient or damages to the gas tubes when the patient moves or changes position, the device is provided with at least one sensor and the holding device is provided with control arrangement for controlling its movements. The sensor detects movement of the patient is connected via the connecting interface, and a signal generated by the sensor and supplied to the control arrangement which, dependent thereon, controls the holding device such that its movements and therefore the movements of the connecting interface automatically follow the movements of the patient.

12 Claims, 3 Drawing Sheets

DEVICE FOR THE SUPPLY OF A GAS FROM A RESPIRATOR/ANAESTHESIA DEVICE TO A BEDRIDDEN PATIENT

BACKGROUND OF THE INVENTION

1. Field of the Invention

The present invention is directed to a device for supplying a gas from a respirator/anaesthesia device to a bedridden patient, of the type having at least one gas tube and a connecting interface that can be connected to the patient, as well as an adjustable holding device for the gas tube and for the connecting interface.

2. Description of the Prior Art

A device of this general type is described in the brochure of Siemens with the title: "Servo Ventilator 900 E". Here, the connecting interface is a tracheotomy tube that is introduced into the respiratory tract of the patient subsequent to making an incision at the throat of the patient. The coupling part of the connecting interface, in this case the part that projects from the throat, is provided with a wing-shaped collar, which is held close at the throat by a fastening strap that is fastened in the collar wings and that is arranged around the throat. The holding device that carries the expiration tubes, the inspiration tubes and a Y-shaped tube, which connects the aforementioned tubes to the coupling part, is a multi-part arm, whose parts can be mutually adjusted with the aid of a bolted connection. The holding device is adjusted such that it is fixed in an appropriate position for the patient. If the patient moves or changes position, it is possible that the tracheotomy tube may press against the sensitive walls of the throat incision. Given repeated or jerky movements, the tracheotomy tube can be dislodged out of its position. The gas tube that is connected to the coupling part also may be strained.

A further known device of the type described above is described in the magazine "Critical Care News" No. 7–8 published by the company Siemens, pages 8 and 11. The device differs that in the aforementioned Siemens brochure in that the connecting interface is an endotracheal tube that is conducted into the mouth cavity and into the respiratory tract of the patient. If the patient moves, the tube can be dislocated and can thereby damage the mucosa in the respiratory tract.

In intensive care, it is conventional to attach a face mask to a patient for connection to a respirator. A face mask is also utilized when the patient is connected to an anaesthesia device. The face mask is normally attached to the patient with the aid of a strap. A disadvantage is that head movements can cause a leakage between the mask and the surrounding facial area. This is a significant problem requiring constant attention on the part of the hospital nursing personnel.

SUMMARY OF THE INVENTION

An object of the present invention is to provide a device of the type described above, which prevents leaks, injury to the patient, and damage to the gas tubes given a movement or a position change of the patient.

This object is inventively achieved in a device of the above general type which is provided with at least one sensor, and wherein the holding device is provided with control apparatus for controlling its movements, the sensor being fashioned such that it detects a movement of the patient. The patient is connected to the gas tube via the connecting interface, a signal is generated by the sensor and is supplied to the control apparatus, which, dependent thereon, controls the holding device such that its movements, and therefore the movements of the connecting interface, automatically follow the movements of the patient. An appropriate constant force relative to the connecting interface can always be maintained due to the inventive control of the holding device. Given an intubated or a tracheotomized patient, the constant force at the connecting is zero in all positions of the patient. When the patient is provided with a face mask, an appropriate constant pressure in all positions of the patient is inventively maintained with the aid of the holding device, so that a close fit of the face mask against the patient is always present.

According to the invention, the sensor can be attached at the holding device, at the gas tube or at the connecting interface.

In an advantageous embodiment of the invention, the holding device has at least one first arm and at least one second arm, with one end of the first arm being connected to a stationary part and its opposite second end being connected to one end of the second arm. The other end of the second arm is connected to the gas tube and/or to the connecting interface. As a result of the holding device being composed of only two arms, a relatively stable holding device is achieved.

According to the invention, the first arm of the holding device is preferably rotatable around its longitudinal axis.

In a further embodiment of the invention the control apparatus includes a control unit and at least one driving unit, and the sensor signal is supplied to the control unit, which generates a control signal therefrom for the drive unit. Preferably, the drive unit is a motor.

According to the invention, the second arm is preferably pivoted around the second end of the first arm by the driving unit, the pivoting ensuing in a common plane containing both arms.

In another embodiment of the invention the first arm is pivotable in a plane at the end that is connected to the stationary part, this plane being perpendicular to the aforementioned common plane containing both arms.

In a further embodiment of the invention the second arm is bendable (deformable) at least along a larger part of its length. In this embodiment, the second arm can be firmly connected to the first arm, so that a relatively stable holding device results.

The movements of the second arm can be controlled by cables, which run in the inside of the second arm and along its length and which are connected to the drive unit at the proximal end of the second arm. Again, the drive unit is preferably a motor.

DESCRIPTION OF THE PREFERRED EMBODIMENTS

Figure 1:
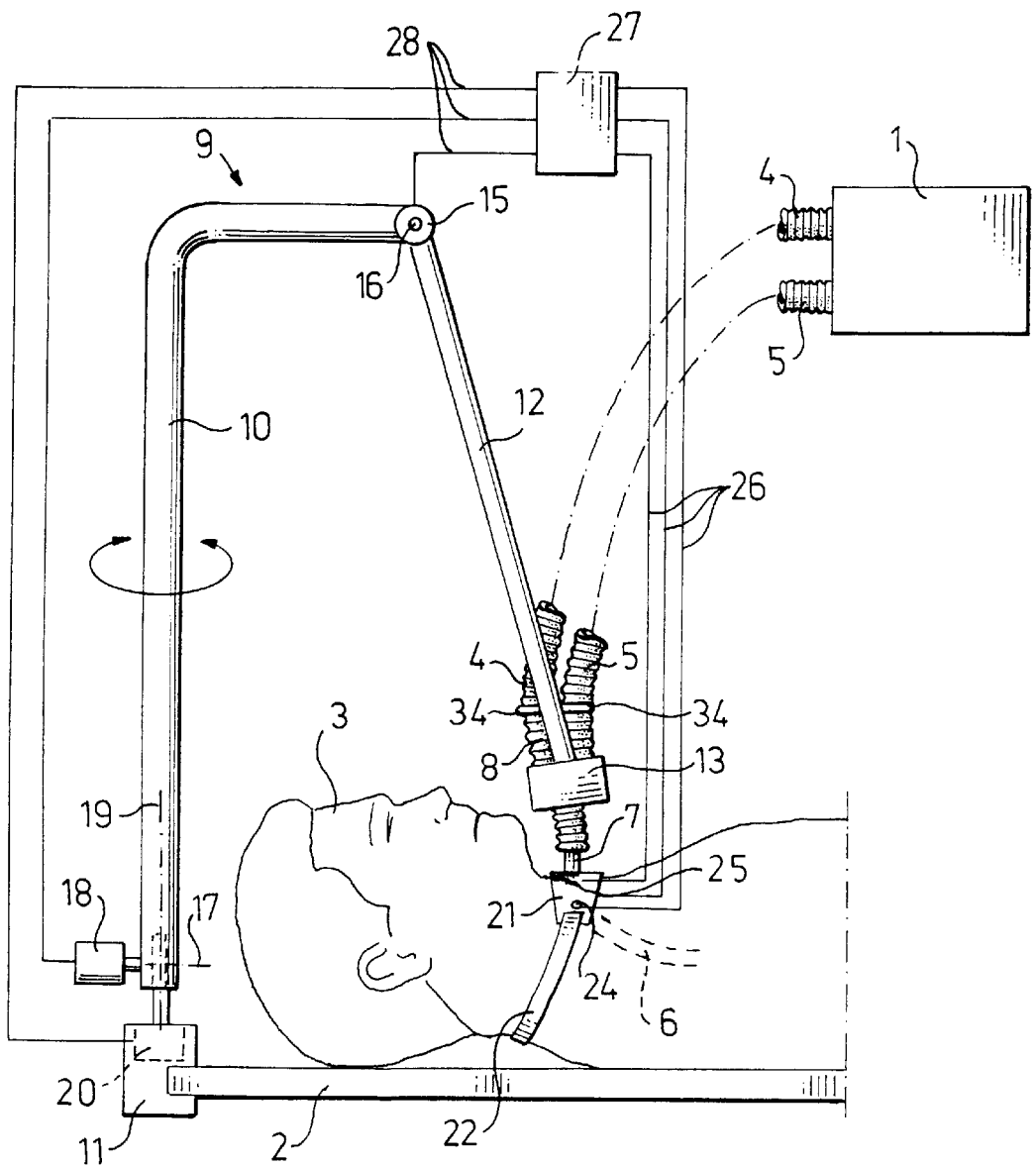
FIG. 1 is a side view, partially in block diagram form, of a device in accordance with the invention.

FIG. 1 shows an arrangement for the supply of a gas from a respirator 1 to a patient 3 lying on a bed 2. The device has an expiration tube 4, an inspiration tube 5, a tracheotomy tube that is introduced through an incision at the throat of the patient 3, and a Y-shaped tube 8 that is attached between the expiration tube 4 and the inspiration tube 5 and the connecting part 7 of the tracheotomy tube 6. The Y-shaped tube 8 is partially tightly connected to the ends of the gas tubes 4, 5 and which if sealed against the connecting part 7. The arrangement also includes a holding device 9 for the gas tubes 4, 5 and 8. The holding device 9 is composed of an L-shaped arm 10, with one end fastened at the bed 2 by a clamp 11 and an opposite end connected to a second arm 12. The free end of the second arm 12 is provided with a ring-shaped coupling 13, in which the tube 8 is held. The second arm 12 is also provided with adapters 34 that embrace the tubes 4 and 5, respectively. A motor 15 is mounted in the connection between the arms 10 and 12. The arm 12 can be pivoted around the axis of this motor 15. This pivoting ensues in a plane in which both the arms 10 and 12 are disposed (here the plane of the drawing). The arm 10 can be pivoted by a motor 18 around an axis 17 perpendicular to the drawing plane and can be rotated around its longitudinal axis by a motor 20.

Figure 2:
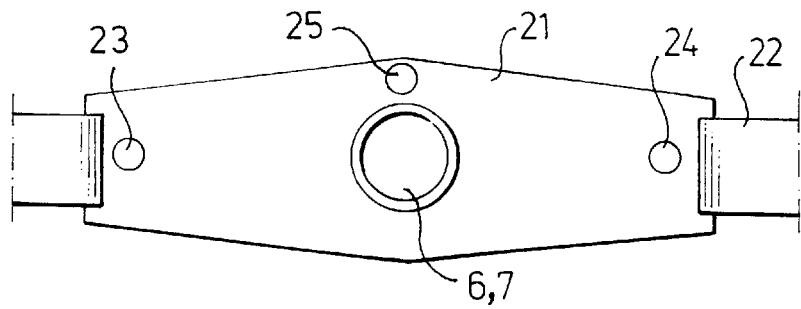
FIG. 2 shows a part of a tracheotomy tube with details according to the invention.

The connecting interface 7 of the tracheotomy tube 6 is provided with a wing-shaped collar 21, which sits closely against the throat of the patient 3, possibly with a compress therebetween. The collar 21 is fastened by means of a strap 22 that extends around the throat of the patient 3. The side of the collar 21 that faces the patient 3 is provided with three sensors 23, 24, 25. The sensor 23 is not shown in FIG. 1. FIG. 2 shows that the sensors 23, 24 are mounted at the respective wing ends of the collar and that the sensor 25 is mounted at the upper edge of the collar, which means close to the chin of the patient given an applied collar. The sensors 23, 24, 25 are connected via connections 26 to a control unit 27 for generating control signals. The control unit 27, in turn, is connected to the motors 15, 18 and 20 via connections 28.

When the patient moves, the pressure sensitive sensors 23, 24, 25 arranged at the collar 21 detect this movement, and each sensor 23, 24, 25 generates a signal that corresponds to the pressure acting on the respective sensor 23, 24, 25. These signals are supplied to the control unit 27 via the connections 26. The control unit 27, in turn, generates control signals that are supplied to the motors 15, 18, 20 via the connections 28. The control signals are dimensioned such that the movements of the arms 10, 12 follow the movements of the patient 3. As a result, the force that the tracheotomy tube 6 exerts against the walls of the throat incision is always zero.

Figure 3:
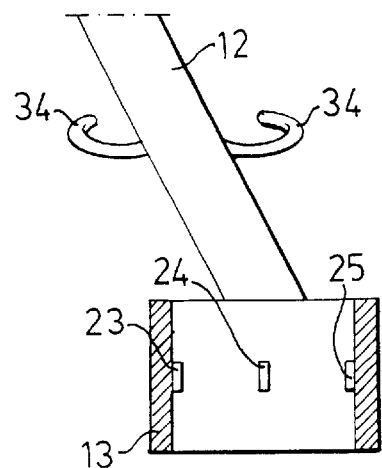
FIG. 3 shows a part of the holding device according to FIG. 1.

In connection with intubation of a patient (not shown), i.e. when an endotracheal tube is introduced through the mouth into the airways, it is inventively provided that the sensors 23, 24, 25 are appropriately arranged at the inner wall of the ring-shaped coupling part 13. Given a tube arranged in the coupling part 13, the sensors 23, 24, 25 can thus detect the movements of the tube in the coupling part 13, which movements correspond to the movements of the endotracheal portion of the tube and therefore the movements of the patient, and can thus control the arms 10, 12 (as has already been described) such that they automatically follow the movements of the patient. FIG. 3 shows such an embodiment. The adapters 34 described in connection with FIG. 1 for the tubes 4, 5 are shown.

Figure 4:
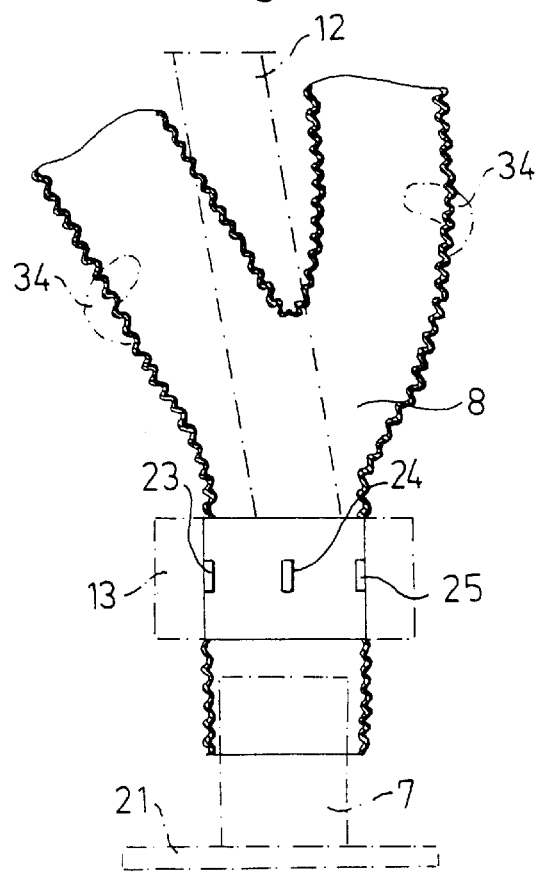
FIG. 4 shows a part of a gas tube according to FIG. 1.

FIG. 4 shows a further embodiment of the invention, wherein the sensors 23, 24, 25 are attached to the tube 8, or are attached to the part of the tube 8 that lies against the inner wall of the coupling part 13 when received therein. The outer wall of the tube 8 is preferably smooth along the section that is arranged in the coupling part 13.

The embodiments wherein the sensors 23, 24,25 are mounted at the tube 8 also can be utilized in connection with a tracheotomized patient.

Figure 5:
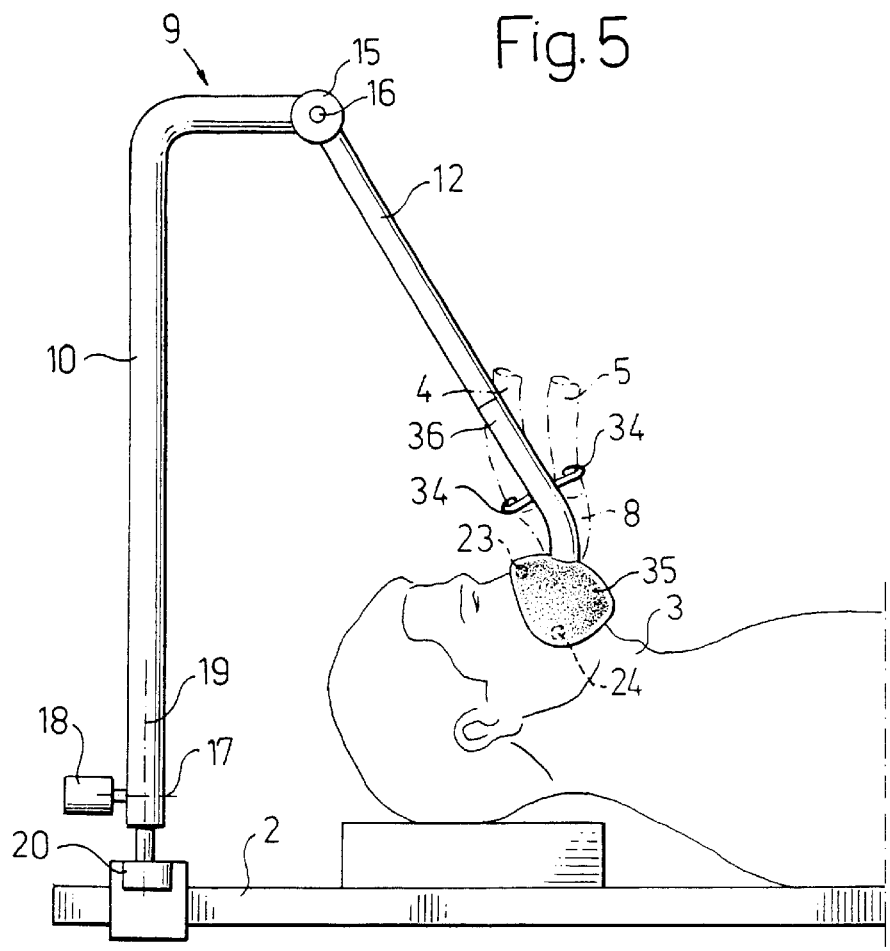
FIG. 5 shows a holding device according to the invention with a face mask for the patient.

FIG. 5 shows a holding device similar to the one that described in connection with FIG. 1. The holding device according to FIG. 5 has a face mask 35 at the distal end. FIG. 5 shows the Y-shaped tube 8 behind the second arm 12, which has an oblique side connection opposite the face mask 35. The sensors 23, 24, 25 are attached against the face of the patient 3 at the sealing surface of the face mask 35. The sensor 25 is preferably mounted at the bridge of the nose of the patient 3 and the other sensors 23, 24 are preferably mounted in the areas of the cheeks of the patient 3. FIG. 5 only shows the sensors 24, 25. The arm 12 exerts a force against the face mask 35 so that it lies against the face of the patient in a gas-tight manner. The movements of the patient 3 are detected by the sensors 23, 24, 25, and the arms 10, 12 and therefore the face mask 35 are controlled in the manner described in connection with FIG. 1, such that they automatically follow the movements of the patient 3. Due to the sensors 23, 24, 25, the pressure of the face mask 35 against the face is continuously detected, so that this pressure is constant for all positions of the patient. The part of the arm 12 that is referenced 36 in FIG. 5 and that is the closest to the face mask 35 is preferably made of a light elastic material, which prevents the pressure of the face mask 35 against the face from exceeding an upper fixed limit in the event that complications arise.

Figure 6:
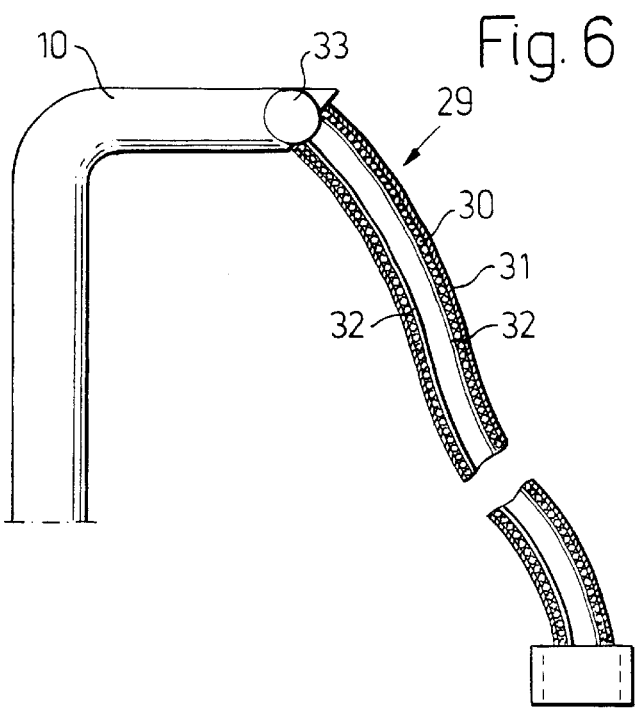
FIG. 6 shows a further embodiment of a holding device according to the invention.

FIG. 6 shows a further exemplary embodiment, wherein the arm 10 is connected to an arm 29, which can be bent (deformed) along its entire length. The core 30 of the arm 29 can be made of a helically wound metal wire and its outer wall 31 can be made of a soft plastic material. The arm 29 has cables 32 that proceed in the inside of the arm 29 along its entire length. The cables 32 are fastened at the distal end of the arm 29. A motor 33 that is connected to the cables 32 is arranged at the proximal end of the arm 29. The cables 32 can be maneuvered by the motor 33 in order to control the movements of the arm 29. In a similar way, two orthogonally arranged motors respectively connected to pairs of cables can be used. As a result, the arm 29 can be controlled relatively exactly. Such an example is not shown in the FIG. 6. This arm 29 can replace the second arm 12 that has already been shown in connection with FIGS. 1 and 5.

In the invention, the control of the arm 10 is possible without the motors 18 and 20, with only an electrical control of the motors 16 or, 33 (FIG. 6) being necessary. The arm 29 shown in FIG. 6 can also be hydraulically or pneumatically controlled using an electromagnet or by means of piezo-rods, memory metals or bi-metals.

The number of sensors is not limited to three but can be more or less than this number depending on the need. The positions of the sensors are not limited to the positions shown in connection with the figures, but can be applied at appropriate places for further specific purposes.

When the patient is connected to an anaesthesia device, the control signals of the sensors can provide an indication with respect to the depth of the narcosis; this can be of diagnostic importance or of practical importance for the physician.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for supplying gas from a respirator/anaesthesia device to a bedridden patient, comprising:

a gas tube having a first end adapted for connection to said respirator/anaesthesia device, and a second end;

a connecting interface connected to said second end of said gas tube and adapted for connection to a bedridden patient to supply gas thereto;

an adjustable, movable holder coupled to said gas tube for supporting said gas tube;

a control arrangement connected to said holder for controlling movement thereof; and a sensor which detects movement of said patient and which emits a sensor signal dependent on said movement; and said sensor being connected to said control arrangement and supplying said sensor signal thereto and said control arrangement, dependent on said sensor signal, controlling movement of said holding device so that movement of said connecting interface coupled to said holding device follows said movement of said patient.

2. An apparatus as claimed in claim 1 wherein said sensor is mounted at said holder.

3. An apparatus as claimed in claim 1 wherein said sensor is mounted at said gas tube.

4. An apparatus as claimed in claim 1 wherein said sensor is mounted at said connecting interface.

5. An apparatus as claimed in claim 1 wherein said holder comprises a stationary part, a first arm with first and second opposite ends and a second arm with first and second opposite ends, said first end of said first arm being connected to said stationary part and said second end of said first arm being connected to said first end of said second arm, and said second end of said second arm being connected to an element selected from the group consisting of said gas tube and said connecting interface.

6. An apparatus as claimed in claim 5 wherein said first arm has a longitudinal axis, and wherein said first arm is rotatable around said longitudinal axis under control of said control arrangement.

7. An apparatus as claimed in claim 5 wherein said control arrangement comprises a control unit, supplied with said sensor signals, and at least one drive unit electrically connected to said control unit and interacting with said holder to move said holder, said control unit generating a control signal dependent on said sensor signal and supplying said control signal to said drive unit to move said holder.

8. An apparatus as claimed in claim 7 wherein said second end of said first arm and said first end of said second arm are connected by a pivoting connection, and wherein said first arm and said second arm are disposed in a common plane, and wherein said drive unit interacts with said holder to pivot said first and second arms at said pivotable connection relative to each other in said common plane.

9. An apparatus as claimed in claim 8 wherein said first end of said first arm is connected to said stationary part by a further pivotable connection, allowing pivoting of said first arm in a plane disposed perpendicularly to said common plane, and wherein said drive unit interacts with said first arm to pivot said first arm relative to said stationary part at said further pivotable connection.

10. An apparatus as claimed in claim 7 wherein said second arm is comprised of material allowing bending of said second arm at least along a majority portion of a length of said second arm.

11. An apparatus as claimed in claim 10 wherein said second arm contains a plurality of cables proceeding in an interior of said second arm and extending along said length of said second arm, said cables being connected to said drive unit at said first end of said second arm.

12. An apparatus as claimed in claim 7 wherein said drive unit comprises a motor.

* * * * *